(12) United States Patent
Kavuru

(10) Patent No.: US 11,535,644 B2
(45) Date of Patent: Dec. 27, 2022

(54) SOLID-STATE FORMS OF REGADENOSON, THEIR USE AND PREPARATION

(71) Applicant: JOHNSON MATTHEY PUBLIC LIMITED COMPANY, London (GB)

(72) Inventor: Padmini Kavuru, Devens, MA (US)

(73) Assignee: Macfarlan Smith Limited, Edinburgh (GB)

( * ) Notice: Subject to any disclaimer, the term of this patent is extended or adjusted under 35 U.S.C. 154(b) by 151 days.

(21) Appl. No.: 16/948,659

(22) Filed: Sep. 28, 2020

(65) Prior Publication Data

US 2021/0009626 A1    Jan. 14, 2021

Related U.S. Application Data

(63) Continuation of application No. PCT/US2019/024518, filed on Mar. 28, 2019.

(60) Provisional application No. 62/649,843, filed on Mar. 29, 2018.

(51) Int. Cl.
*C07H 19/19*    (2006.01)

(52) U.S. Cl.
CPC .......... *C07H 19/19* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,403,567 B1 | 6/2002 | Zablocki et al. |
| 6,642,210 B1 | 11/2003 | Zablocki et al. |
| 7,144,872 B2 | 12/2006 | Zablocki et al. |
| 7,655,637 B2 | 2/2010 | Zablocki et al. |
| 7,671,192 B2 | 3/2010 | Zablocki et al. |
| 7,732,595 B2 | 6/2010 | Zablocki et al. |
| 7,956,179 B2 | 6/2011 | Zablocki et al. |
| 8,106,183 B2 | 1/2012 | Zablocki et al. |
| 8,268,988 B2 | 9/2012 | Zablocki et al. |
| 8,278,435 B2 | 10/2012 | Zablocki et al. |
| 8,524,883 B2 | 9/2013 | Zablocki et al. |
| 8,859,522 B2 | 10/2014 | Wooldridge et al. |
| 9,085,601 B2 | 7/2015 | Zablocki et al. |
| 9,441,006 B2 | 9/2016 | Kvapil et al. |
| 9,771,390 B2 | 9/2017 | Zhang et al. |
| 9,809,617 B2 | 11/2017 | Liu et al. |
| RE47,301 E | 3/2019 | Zablocki et al. |
| RE47,351 E | 4/2019 | Zablocki et al. |
| 2014/0194615 A1 | 7/2014 | Kvapil et al. |
| 2016/0024137 A1* | 1/2016 | Grisenti ............... C07H 19/167 536/27.4 |
| 2016/0115191 A1 | 4/2016 | Rangisetty et al. |
| 2016/0244474 A1 | 8/2016 | Kovi et al. |
| 2016/0304551 A1 | 10/2016 | Zhang et al. |
| 2017/0002036 A1 | 1/2017 | Liu et al. |
| 2018/0127452 A1 | 5/2018 | Kovi et al. |

FOREIGN PATENT DOCUMENTS

| | | |
|---|---|---|
| CN | 104513241 A | 4/2015 |
| CN | 104744540 A | 7/2015 |
| CN | 105085593 A | 11/2015 |
| CN | 105175468 A | 12/2015 |
| CN | 105198950 A | 12/2015 |
| WO | 2014068589 A2 | 5/2014 |
| WO | 2014177119 A1 | 11/2014 |
| WO | 2014207758 A2 | 12/2014 |
| WO | 2016126734 A1 | 8/2016 |
| WO | 2017042837 A2 | 3/2017 |
| WO | WO-2017042937 A1 * | 3/2017 |

* cited by examiner

*Primary Examiner* — Traviss C McIntosh, III

(57) ABSTRACT

The invention relates to a crystalline methanol or dimethyl sulfoxide solvated form of regadenoson and an anhydrous polymorph of regadenoson. The invention is also directed to the preparation of the methanol or dimethyl sulfoxide solvated and anhydrous solid-state forms of regadenoson. In particular, the invention relates to the preparation of the anhydrous polymorph of regadenoson in a stable form from the dimethyl sulfoxide solvated form of regadenoson, which preparation is purifiable and scalable.

13 Claims, 14 Drawing Sheets

SOLID-STATE FORMS OF REGADENOSON, THEIR USE AND PREPARATION

CROSS-REFERENCE TO RELATED APPLICATIONS

This application is a continuation of International Application No. PCT/US2019/024518, filed Mar. 28, 2019, which claims priority to U.S. Provisional Patent Application No. 62/649,843, filed Mar. 29, 2018, the disclosures of which are incorporated herein by reference in their entireties for all purposes.

FIELD OF THE INVENTION

The invention relates to a crystalline methanol (MeOH) and dimethyl sulfoxide solvated and anhydrous solid-state forms of Regadenoson (RDN), the preparation of the aforesaid forms and their use.

BACKGROUND OF THE INVENTION

RDN, 1-[6-amino-9-[(2R,3R,4S,5R)-3,4-dihydroxy-5-(hydroxymethyl)oxolan-2-yl]purin-2-yl]-N-methylpyrazole-4-carboxamide, of the formula I below, is an

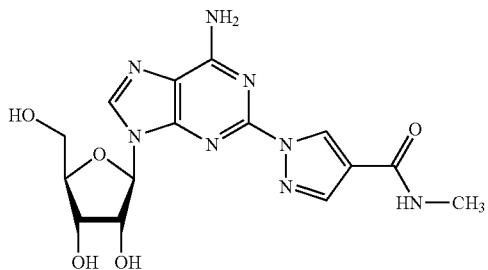

A2A adenosine receptor agonist that is a coronary vasodilator that is commonly used in pharmacologic stress testing. It is useful for radionuclide myocardial perfusion imaging as it produces hyperemia quickly and maintains it for a useful duration. It preferable to other stress agents such as adenosine, which are less selective and therefore cause more side-effects, than RDN.

The preparation of RDN is disclosed in U.S. Pat. No. 6,642,210, but it does not disclose the existence of any polymorphic form. U.S. Pat. No. 9,085,601 discloses monohydrate of RDN. WO2017042837 discloses an anhydrous Form S of RDN having XRPD peaks at 10.3, 10.8, 19.0, 21.6 and 25.5 2Θ. U.S. Pat. No. 9,441,006 discloses polymorph E of RDN having XRPD peaks 5.8, 12.3, 15.9, 17.3, 20.5, 22.6, 23.6, 27.7 and 29.2 2Θ and DSC endotherm at 260.7° C. or 259.3° C. U.S. Pat. No. 9,809,617 discloses a polymorph E of RDN having endotherm at 221.2° C. US Patent application 20160024137 discloses trifluoroethanol and ethanol solvate polymorphs, and anhydrous polymorph of RDN, wherein the anhydrous polymorph having XRPD peaks at 8.24, 14.9, 17.7, 18.2, 19.8, 21.9, 26.2, 27.7 and 30.4 2Θ and a DSC endotherm event at 264.4° C. CN105175468 application discloses a polymorph B of RDN having a DSC endotherm event at 220.0° C. and TGA endotherm events at 109.5° C. 9.81%; 14.61% weight loss at 175.1° C. CN105198950 application discloses a polymorph E of RDN having a DSC endotherm event at 173.7° C. and TGA endotherm events at 80° C., 5.3% weight loss, and at 182.2° C., 4.5% weight loss. U.S. Pat. No. 8,859,522 discloses a monohydrate polymorph of RDN. US Patent application 20160244474 discloses a polymorph H of RDN, having XRPD peaks at 6.2, 10.3, 10.7 and 25.5 2Θ and a DSC endotherm event at 271.3° C. U.S. Pat. No. 7,732,595 discloses a monohydrate of RDN (Form A) having a DSC endotherm event at 194.7° C., and Forms B and C of RDN. U.S. Pat. No. 9,624,258 discloses a propylene glycol solvate of RDN having XRPD peaks at 9.1, 18.0, 22.8 and 25.5 2Θ and a TGA having four endotherm events. None of the references disclose a MeOH or DMSO solvated form of RDN. None of the references also show an anhydrous polymorph of RDN prepared from a DMSO solvated form of RDN.

SUMMARY OF THE INVENTION

The invention relates to a crystalline MeOH or DMSO solvated form of RDN and an anhydrous polymorph of RDN prepared from a DMSO solvated form of RDN. The invention is also directed to the preparation of the aforesaid solvated and anhydrous solid-state forms of RDN.

DETAILED DESCRIPTION OF THE INVENTION

Figure 1:
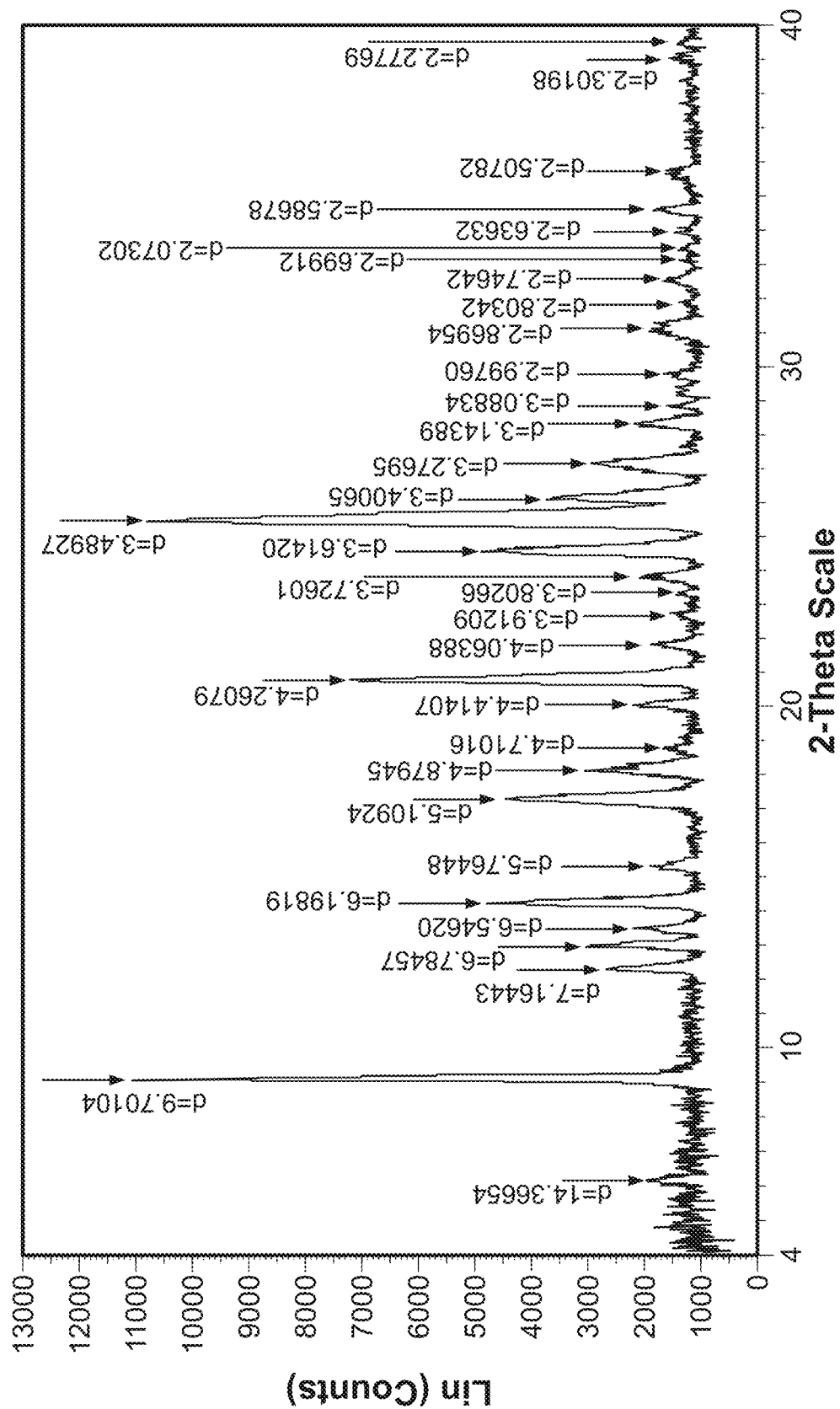
FIG. 1 is an XRPD pattern of crystalline solid-state Form I of methanol solvate of RDN.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are not intended to be limited to the examples described herein and shown, but are to be accorded the scope consistent with the claims.

The term "solid-state form" of RGN, as used herein, includes crystalline or polymorphic forms, amorphous phases, and solvates.

The use of the term "about" or the symbol "~" includes and describes the value or parameter per se. For example, "about x" includes and describes "x" per se. The term "about" when used in association with a measurement, or used to modify a value, a unit, a constant, or a range of values, refers to variations of +/−5 percent.

The term "substantially" or "substantially free/pure" with respect to a solid-state form means that the form contains about less than 30 percent, about less than 20 percent, about less than 15 percent, about less than 10 percent, about less than 5 percent, or about less than 1 percent by weight of impurities. Impurities may, for example, include other polymorphic forms, water and solvents other than that in the crystalline solid-state form.

The term "room temperature" is defined as a temperature between 15-29° C.; preferably between 20-23° C.

The term "to dry/drying/dried", as used in this patent application, means to dry/drying/dried at 45° C. and under vacuum.

All ranges recited herein include the endpoints. Terms such as "about," "generally," and "substantially," are to be construed as modifying a term or value such that it is not an absolute. This includes, at very least, the degree of expected experimental error, technique error and instrument error for a given technique used to measure a value.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

Embodiments

It is therefore an object of the present invention to provide MeOH or DMSO solvated forms of RDN and an anhydrous polymorph of RDN prepared from a DMSO solvated form of RDN that are purifiable, stable and scalable. It is also the object of the present invention to provide MeOH or DMSO solvated forms of RDN and an anhydrous polymorph of RDN prepared from a DMSO solvated form of RDN that is capable of being isolated and handled. It is further an object of the present invention to provide a process for the preparation of such MeOH or DMSO solvated forms of RDN and anhydrous polymorph of RDN prepared from a DMSO solvated form of RDN; particularly wherein the RGN therein is purified, more especially substantially free/pure. It is yet another object of the invention to use MeOH or DMSO solvated forms of RDN and an anhydrous polymorph of RDN prepared from a DMSO solvated form of RDN to prepare a pharmaceutical dosage form of RDN.

RGD is dissolved in hot (about 50-60° C., more preferred 60° C.) MeOH to yield a saturated methanol solution of RDN. The saturated methanol solution of RDN is then slowly evaporated to yield solid-state Form I of methanol solvate of RDN. Clear, colorless crystals are isolated by filtration.

RDN is slurried in MeOH (~100:1—wt(mg)$_{RDN}$:v(mL)$_{MeOH}$) at about 5° C. for 18-20 h. The slurried RDN is then filtered and dried at 40-50° C., more preferred 45° C., to yield solid-state Form II of methanol solvate of RDN.

RDN is dissolved in DMSO (~100:1—wt(mg)$_{RDN}$:v(mL)$_{DMSO}$) to form a solution of RDN in DMSO. Acetone is then added to the solution of RDN in DMSO (~2:1—v$_{Ace}$:v$_{DMSO}$). The solution of RDN in DMSO is stirred for one day (18-20 h) at room temperature and then the solution of RDN in DMSO is stirred for about 48 h at 5-10° C., more preferred 5° C., to precipitate solid-state Form I of DMSO solvate of RDN.

RDN is dissolved in DMSO (~100:1—wt(mg)$_{RDN}$:v(mL)$_{DMSO}$) to form a solution of RDN in DMSO. Methanol (~1.5:1—v$_{MeOH}$:v$_{DMSO}$) or ethyl acetate (~1:1—v$_{AcOEt}$:v$_{DMSO}$) is then added to the solution of RDN in DMSO. The solution of RDN in DMSO is stirred for about three days (72 h) and then dried under reduced pressure (about −30 mm of Hg) with warming at about 40-50° C., more preferred 50° C. to yield solid-state Form I of DMSO solvate of RDN.

RDN is dissolved in DMSO (~210:1—wt(mg)$_{RDN}$:v(mL)$_{DMSO}$) at about 45-55° C., more preferred 50° C., until a clear solution of RDN in DMSO is obtained. To the clear DMSO solution, ethyl acetate (~1:3—v$_{DMSO}$:v$_{EtOAc}$) is added slowly and left stirring at about 20-27° C., more preferred 25° C., for about 18-20 h to yield a precipitate. The precipitate is filtered, washed with ethyl acetate (~1:1—v$_{DMSO}$:v$_{EtOAc}$) and dried under vacuum at (about −30 mm of Hg) about 40-50° C., more preferred 45° C., to yield solid-state Form II of DMSO solvate of RDN.

RDN is dissolved in DMSO (250:1—wt(mg)$_{RDN}$:v(mL)$_{DMSO}$) with stirring at about 45-55° C., more preferred 50° C., to yield a clear solution of RDN in DMSO. Then is sequentially added ethyl acetate (~1:1—v$_{DMSO}$:v$_{EtOAc}$), seeds of solid-state Form II of DMSO solvate of RDN (~1:0.04—wt$_{RDN}$:wt$_{RDNseed}$), and ethyl acetate (~1:4—v$_{DMSO}$:v$_{EtOAc}$). After the additions, heating is stopped and solution is stirred for about 5 hours. The solution is filtered, isolated solid is split in half, and half of the solid is dried under reduced pressure (about −30 mm of Hg) at 55-65° C., more preferred 60° C., to yield solid-state Form I of anhydrous RDN.

In another general aspect, is the use of a solid-state form of RDN according to the invention for use in preparing a pharmaceutical composition; more particularly where the composition is a solution together with one or more pharmaceutically acceptable ingredients.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present invention and the invention is not intended to be limited to the examples described herein and shown.

EXAMPLES

Analytical Experimental

XRPD (X-Ray Powder Diffractometry)

Diffractograms are obtained with laboratory diffractometer, BRUKER D-8 Advance diffractometer, using radiation CuKα (λ=1.542 Å), and Lynxeye super speed detector.

Relative intensities for peak values can vary depending on several factors, including sample preparation, mounting, and analytical procedure and settings of the instrument that is used to obtain the spectrum.

SCXRD (Single Crystal X-Ray Diffraction) is obtained using either PILATUS3 X CdTe 1M detector at Beamline 15-ID-B of ChemMatCARS or Bruker D8 Venture PHOTON 100 CMOS diffractometer equipped with a CuKα INCOATEC Imus micro-focus source (λ=1.54178 Å).

DSC (Differential Scanning calorimetry)

Polymorph Solid-State Form:

DSC measurements are performed on a calorimeter, TA Instruments Q2000 and RSC40.

The sample are weighed in aluminum pans. Investigations were performed in a temperature range of 20-320° C. with a heating rate of 10° C./min, purging with nitrogen at a flow rate of 50 mL/min.

Analysis—TGA (Thermo Gravimetric Analysis)

TGA measurements are recorded using TA Q500 instrument. The samples are weighed in aluminum pans. TGA investigations are performed at a heating rate of 10.0° C./min over a temperature range of 30-300° C., purging with nitrogen at a flow rate of 60 mL/min.

Analysis—$^1$H NMR $^1$H NMR measurements are recorded using Bruker 300 MHz Advance NMR spectrometer in DMSO-d6.

I. Solid-State Form I of Methanol Solvate of RDN

Single crystals of solid-state Form I of the methanol solvate of RDN are made by dissolving around 10 mg of RDN in hot MeOH to form saturated methanol solution of RDN. The saturated methanol solution of RDN is then slowly evaporated to yield clear, colorless crystals of solid-state Form I of methanol solvate of RDN that are isolated by filtration.

The XRPD (FIG. 1) is directed to the solid-state Form I of methanol solvate of RDN, and 2Θ, d-spacing and relative % intensity values for peaks are shown in Table I.

TABLE I

| Angle 2Θ | d value Angstrom | Intensity % |
|---|---|---|
| 6.2 | 14.367 | 17 |
| 9.1 | 9.701 | 100 |
| 12.3 | 7.164 | 24.1 |
| 13.0 | 6.785 | 26.3 |
| 13.5 | 6.546 | 19.6 |
| 14.3 | 6.198 | 43.1 |
| 17.3 | 5.109 | 40.2 |
| 18.2 | 4.879 | 27.1 |
| 18.8 | 4.710 | 15.2 |
| 20.1 | 4.414 | 19.5 |
| 20.8 | 4.261 | 64.8 |
| 21.9 | 4.064 | 17.1 |
| 23.9 | 3.726 | 18.7 |
| 24.6 | 3.614 | 44.2 |
| 25.5 | 3.489 | 96.3 |
| 26.2 | 3.401 | 32.9 |
| 27.2 | 3.277 | 26.6 |
| 28.4 | 3.144 | 19.8 |

The angle measurements are ±0.2° 2Θ. Key defining peaks for solid-state Form I of methanol solvate of RDN include 9.1, 13.0, 14.3, 17.3, 18.2, 20.8, 24.6 and 25.5° 2Θ.

Figure 2:
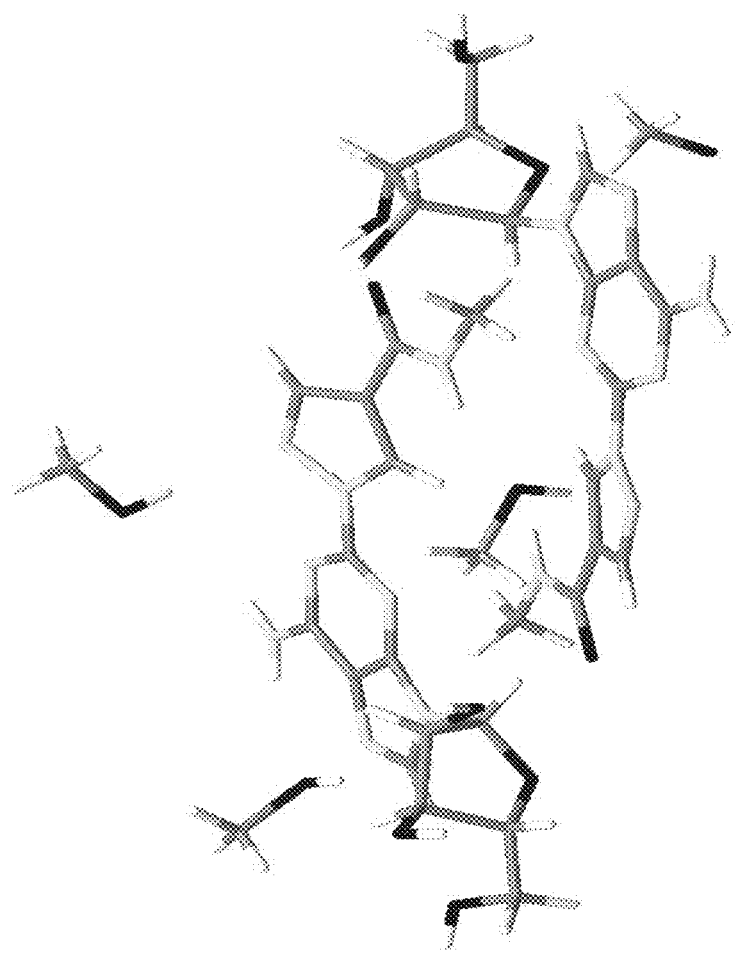
FIG. 2 is a three-dimensional structure of crystalline solid-state Form I of methanol solvate of RDN that is discerned from SCXRD.

FIG. 2 shows the three-dimensional structure of crystalline solid-state Form I of methanol solvated RDN that is discerned from SCXRD. Single crystal parameters for the solid-state Form I of methanol solvated RDN as determined by SCXRD are:

Crystal system, space group=monoclinic, C2
a=20.2462 (18) Å
b=6.9115 (6) Å
c=44.061 (4) Å
α=90°
β=99.979 (2)°
γ=90°
Cell Volume=6072.24 Å$^3$ II. Solid-State Form II of Methanol Solvate of RDN 100 mg of RDN is slurried in 1 mL of MeOH at about 5° C. for 20 h. The slurried RDN is then filtered and dried at 45° C., to yield solid-state Form II of methanol solvate of RDN.

Figure 3:
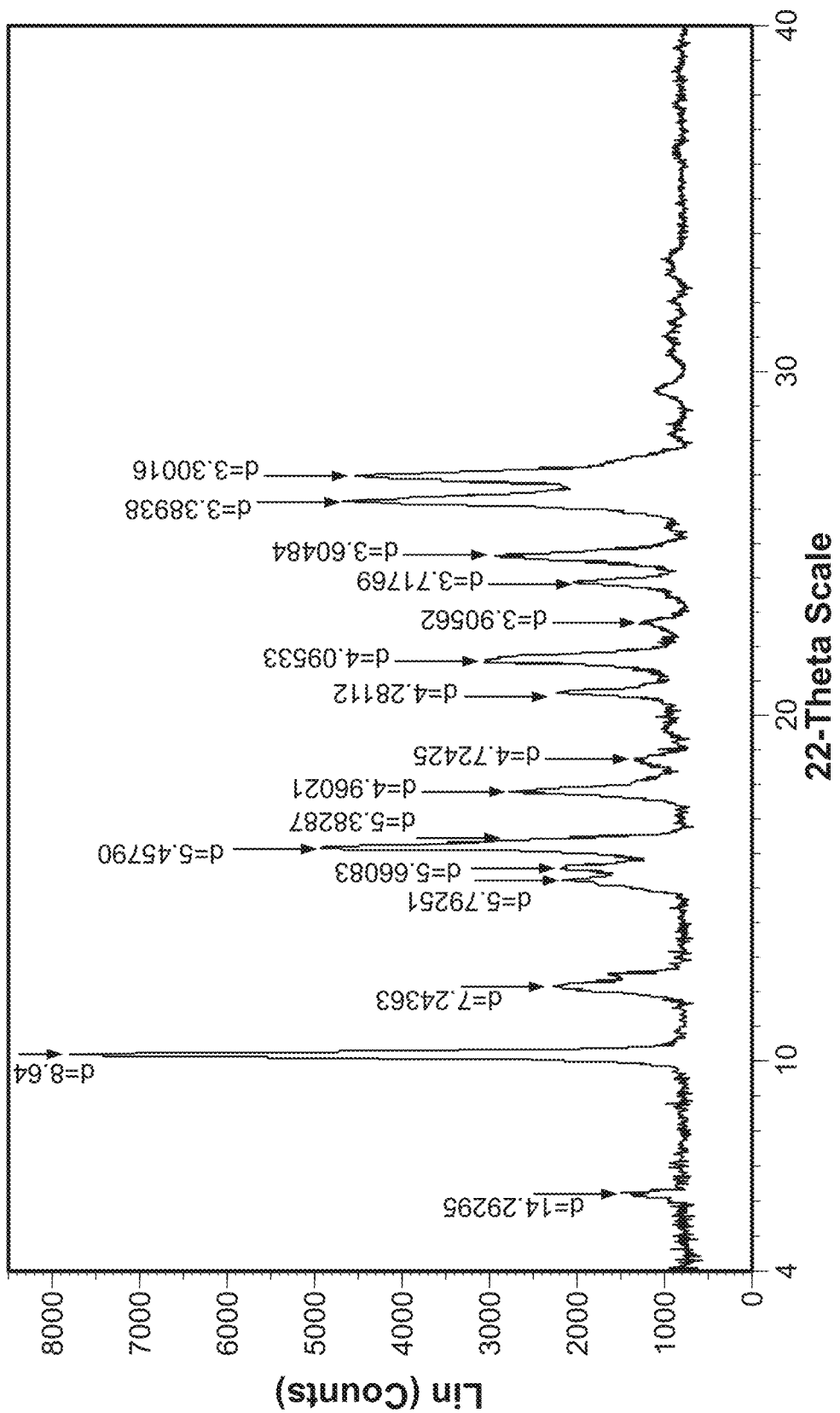
FIG. 3 is an XRPD pattern of crystalline solid-state Form II of methanol solvate of RDN.

The XRPD (FIG. 3) is directed to the solid-state Form II of methanol solvate of RDN, and 2Θ, d-spacing and relative % intensity values for peaks are shown in Table II.

TABLE II

| Angle 2Θ° | d value Angstrom | Intensity % |
|---|---|---|
| 6.2 | 14.293 | 17.9 |
| 10.2 | 8.642 | 100 |
| 12.2 | 7.244 | 28.9 |
| 15.3 | 5.793 | 27.4 |
| 15.6 | 5.661 | 27.9 |
| 16.2 | 5.458 | 63.2 |
| 16.5 | 5.382 | 36.8 |
| 17.9 | 4.960 | 35.5 |
| 18.8 | 4.724 | 16.5 |
| 20.7 | 4.281 | 28.9 |
| 21.7 | 4.095 | 39.2 |
| 22.8 | 3.906 | 16.6 |
| 23.9 | 3.718 | 26.3 |
| 24.7 | 3.605 | 37.3 |
| 26.3 | 3.389 | 59.5 |
| 27.0 | 3.300 | 58.2 |

The angle measurements are ±0.2° 2Θ. Key defining peaks for solid-state Form II of methanol solvate of RDN include 10.2, 12.2, 16.2, 17.9, 21.7, 26.3 and 27° 2Θ.

Figure 4:
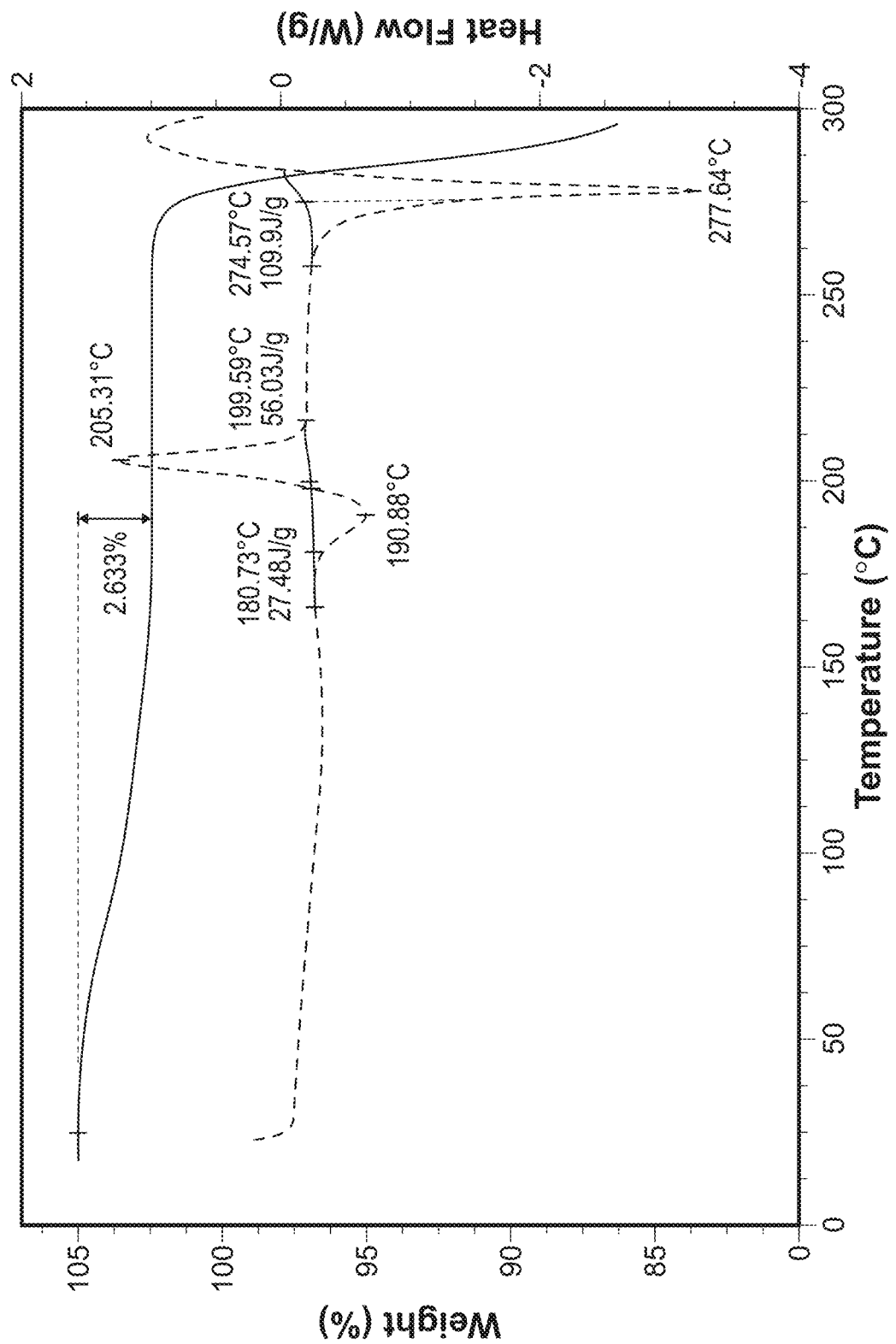
FIG. 4 are DSC and TGA plots of crystalline solid-state Form II of methanol solvate of RDN.

The DSC and TGA plots (FIG. 4) show TGA weight loss of ~2.6% from about 50-150° C. The DSC shows three thermal events at 190.9° C., 205.3° C. and 277.6° C. for the solid-state Form II of methanol solvate of RDN.

Figure 5:
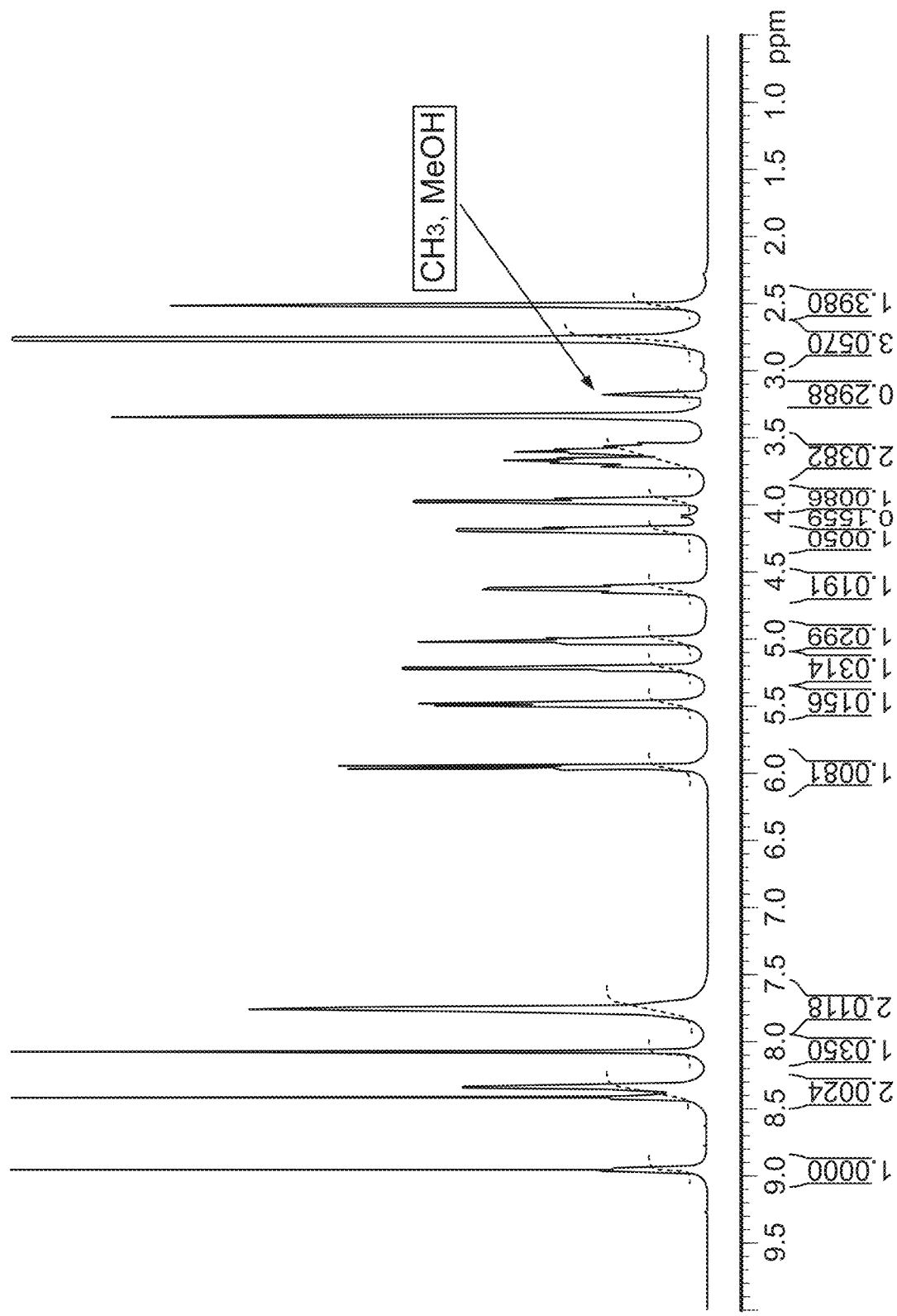
FIG. 5 is a $^1$H NMR spectra of crystalline solid-state Form II of methanol solvate of RDN.

FIG. 5 is directed to the $^1$H NMR for the solid-state Form II of methanol solvate of RDN.

III. Solid-State Form I of Dimethyl Sulfoxide Solvate of RDN 100 mg of the RDN is dissolved in 1 mL DMSO to form a solution of RDN in DMSO. 2 mL of acetone is then added to the solution of RDN in DMSO. The solution of RDN in DMSO is stirred for one day (18-20 h) at room temperature and then 48 h with cooling at 5° C. to precipitate solid-state Form I of DMSO solvate of RDN.

Alternatively, 100 mg of the RDN is dissolved in 1 mL DMSO to form a solution of RDN in DMSO; 1.5 mL of methanol or 1 mL of ethyl acetate is then added to the solution of RDN in DMSO. The solution of RDN in DMSO is stirred for 72 h and then dried under reduced pressure at 50° C. to yield solid state Form I of DMSO solvate of RDN.

Figure 6:
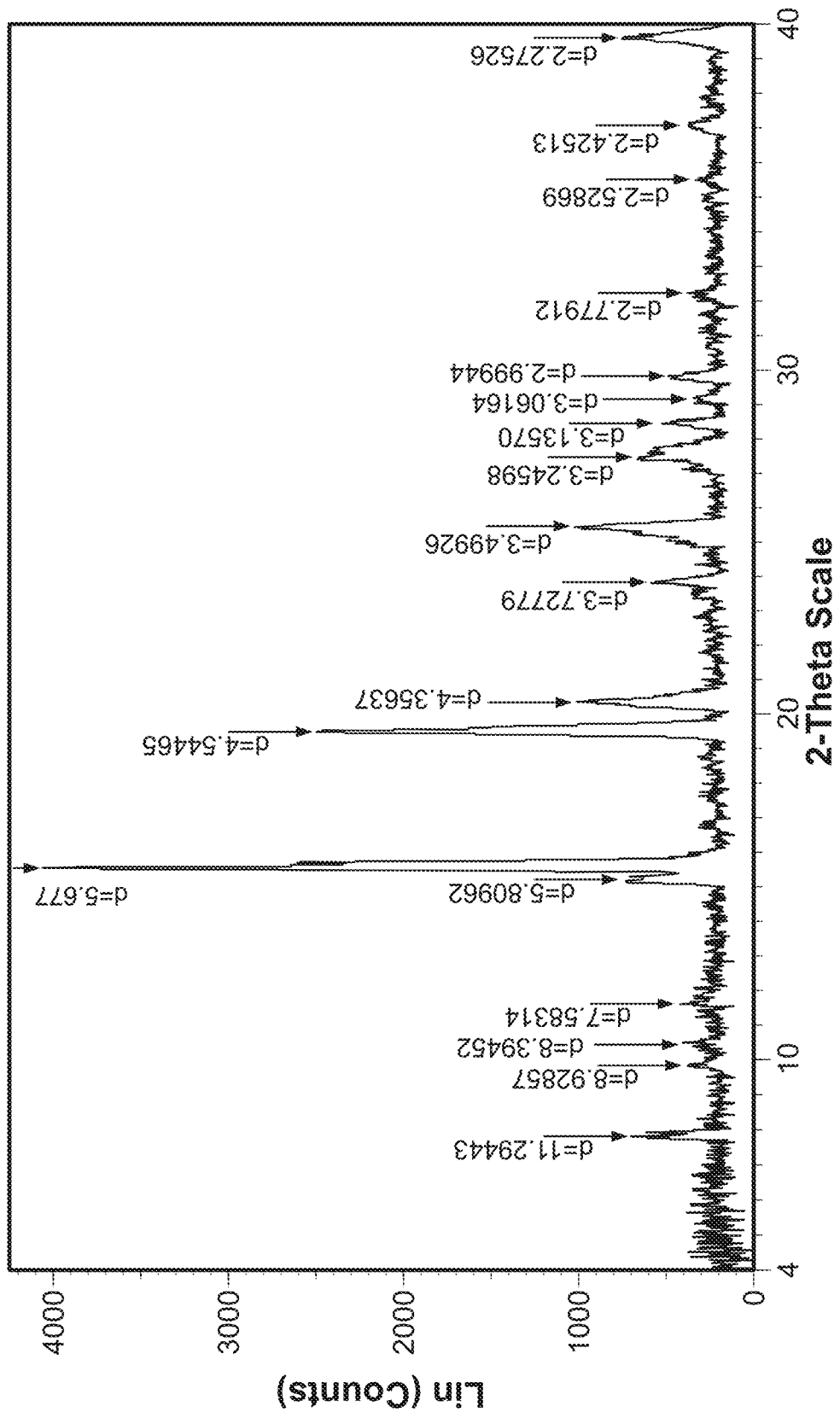
FIG. 6 is an XRPD pattern of crystalline solid-state Form I of DMSO solvate of RDN.

The XRPD (FIG. 6) is directed to the solid-state Form I of DMSO solvate of RDN, and 2Θ, d-spacing and relative % intensity values for peaks are shown in Table III.

TABLE III

| Angle 2Θ° | d value Angstrom | Intensity % |
|---|---|---|
| 7.8 | 11.294 | 16.7 |
| 10.5 | 8.395 | 9.7 |
| 11.7 | 7.563 | 10.3 |
| 15.2 | 5.810 | 17 |
| 15.6 | 5.677 | 100 |
| 19.5 | 4.545 | 61.4 |
| 20.4 | 4.356 | 24.5 |
| 23.9 | 3.728 | 14.3 |
| 25.4 | 3.499 | 24.7 |
| 27.5 | 3.246 | 15.8 |
| 28.4 | 3.136 | 11.6 |
| 29.8 | 2.999 | 11.8 |
| 32.2 | 2.779 | 9.4 |
| 37.0 | 2.425 | 9.2 |
| 39.6 | 2.275 | 18.5 |

The angle measurements are ±0.2° 2Θ. Key defining peaks for solid-state Form I of DMSO solvate of RDN include 15.6, 19.5, 20.4 and 25.4° 2Θ.

Figure 7:
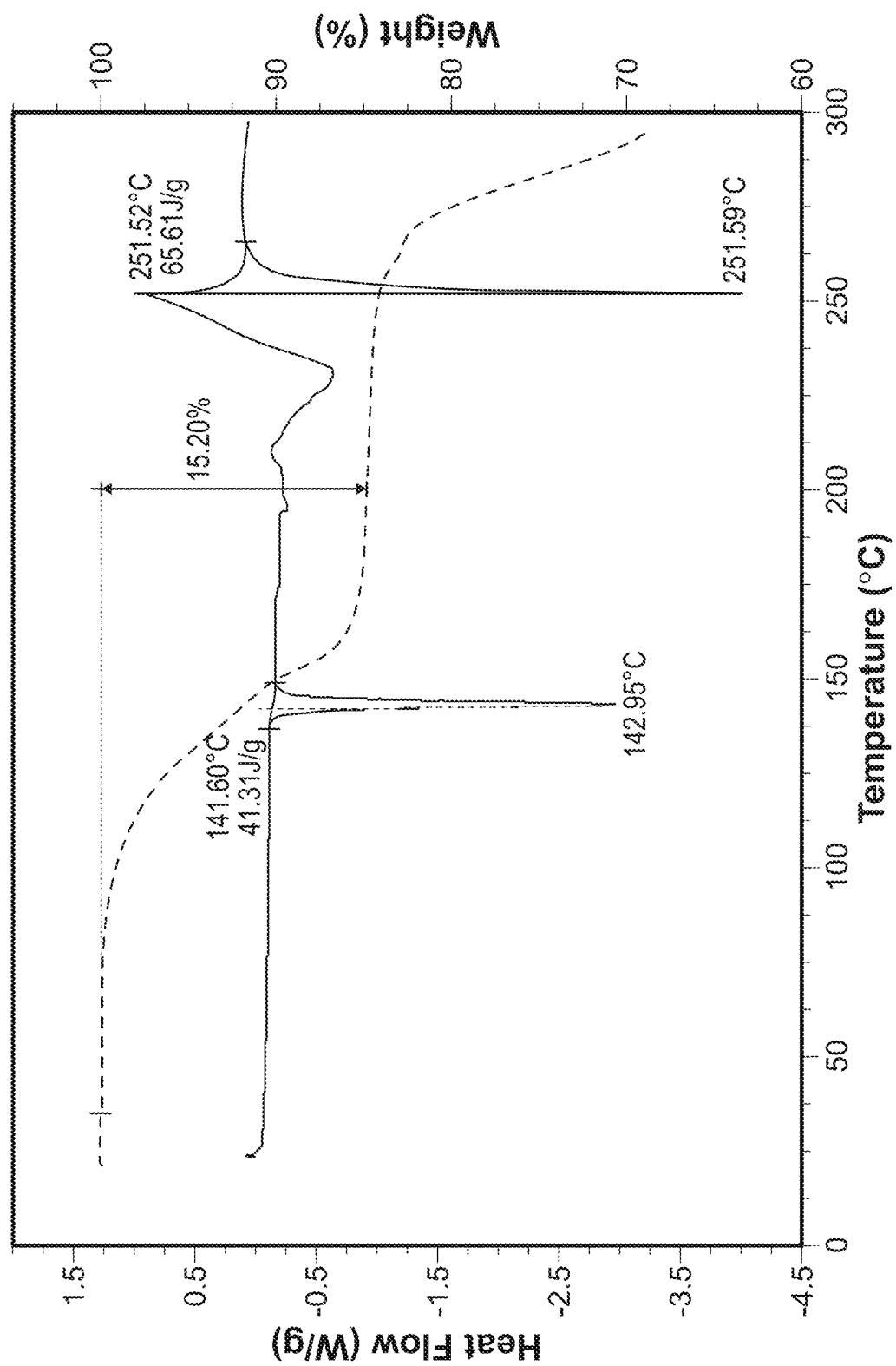
FIG. 7 are DSC and TGA plots of crystalline solid-state Form I of DMSO solvate of RDN.

Single crystal parameters for the solid-state Form I of DMSO solvated RDN as determined by SCXRD are:

Crystal system, space group=orthorhombic, $P2_12_12_1$
a=4.9676(12) Å
b=9.203(2) Å
c=45.667 (11) Å
α=90°
β=90°
γ=90°
Cell Volume=2087.68 Å$^3$ The DSC and TGA plots (FIG. 7) show TGA weight loss of ~16.2% from about 100-150° C., and DSC shows two thermal events at 143.0° C. and 251.6° C. for the solid-state Form I of DMSO solvate of RDN.

Figure 8:
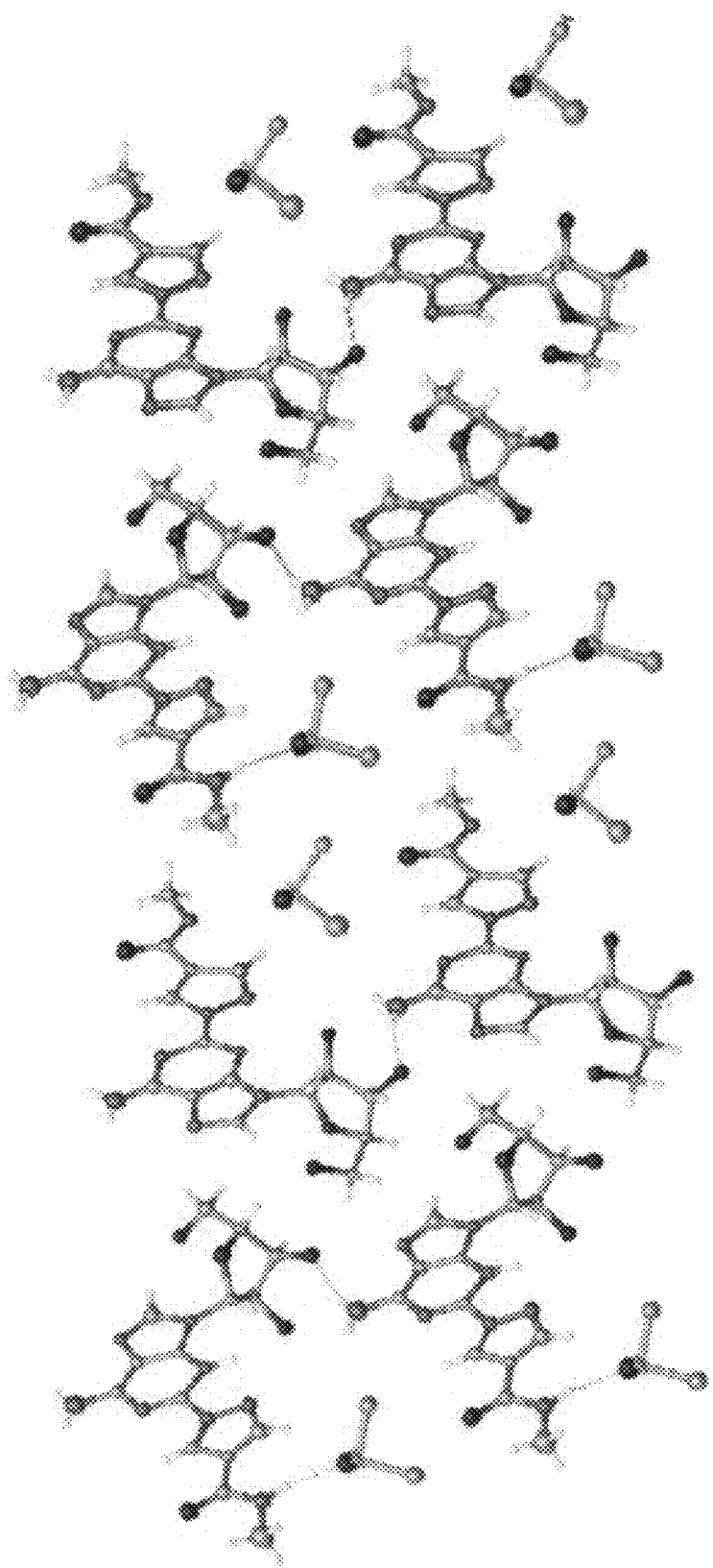
FIG. 8 shows hydrogen bonding between RDN and DMSO in the crystalline solid-state Form I of DMSO solvate of RDN.

FIG. 8 shows hydrogen bonding between RDN and DMSO in the crystalline solid-state Form I of DMSO solvate of RDN.

IV. Solid-State Form II of Dimethyl Sulfoxide Solvate of RDN 1.275 g of RDN is dissolved in 6 mL of DMSO at 50° C. until a clear solution of RDN in DMSO is obtained. To the clear DMSO solution, 20 mL of ethyl acetate is added slowly and the solution is left to stir at room temperature overnight to yield a precipitate. The precipitate is filtered, washed with 5-6 mL of ethyl acetate and dried under vacuum at 45° C. to yield solid-state Form II of DMSO solvate of RDN.

Figure 9:
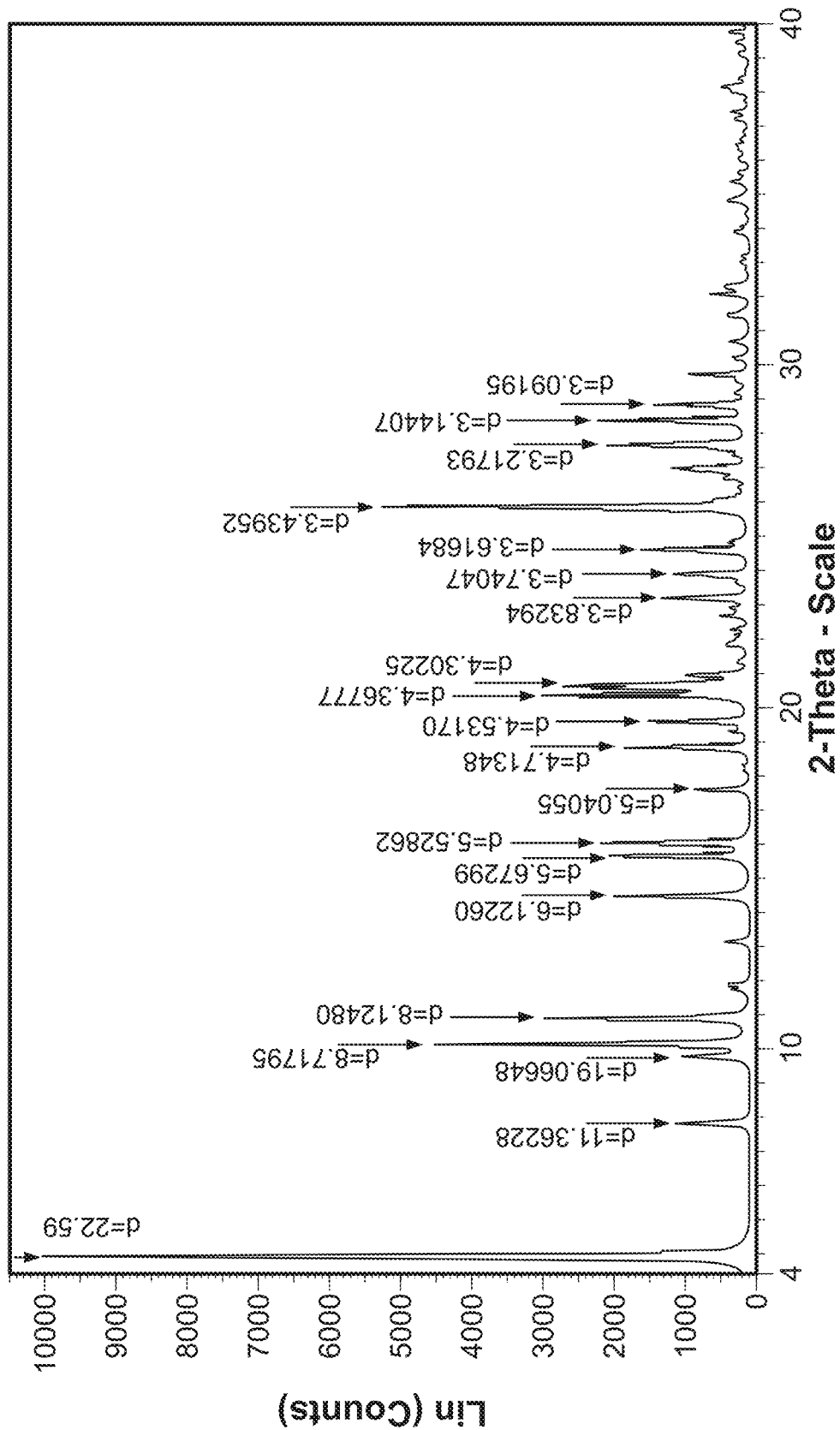
FIG. 9 is an XRPD pattern of crystalline solid-state Form II of DMSO solvate of RDN.

The XRPD (FIG. 9) is directed to the solid-state Form II of DMSO solvate of RDN, and 2Θ, d-spacing and relative % intensity values for peaks are shown in Table IV.

TABLE IV

| Angle 2Θ° | d value Angstrom | Intensity % |
|---|---|---|
| 3.9 | 22.598 | 100 |
| 10.1 | 8.718 | 47.9 |
| 10.9 | 8.125 | 31.9 |
| 14.5 | 6.123 | 22.1 |
| 15.6 | 5.673 | 22.2 |
| 16.0 | 5.529 | 23.2 |
| 17.6 | 5.041 | 9.3 |
| 18.8 | 4.713 | 19.7 |
| 19.6 | 4.532 | 17.8 |

TABLE IV-continued

| Angle 2Θ° | d value Angstrom | Intensity % |
|---|---|---|
| 20.3 | 4.368 | 32.8 |
| 20.6 | 4.302 | 29.8 |
| 24.6 | 3.617 | 17.2 |
| 25.9 | 3.440 | 57.1 |
| 27.7 | 3.218 | 24.6 |
| 28.4 | 3.144 | 24.6 |

The angle measurements are ±0.2° 2Θ. Key defining peaks for solid-state Form II of DMSO solvate of RDN include 3.9, 10.1, 10.9, 16.0, 20.3 and 25.9° 2Θ.

Figure 10:
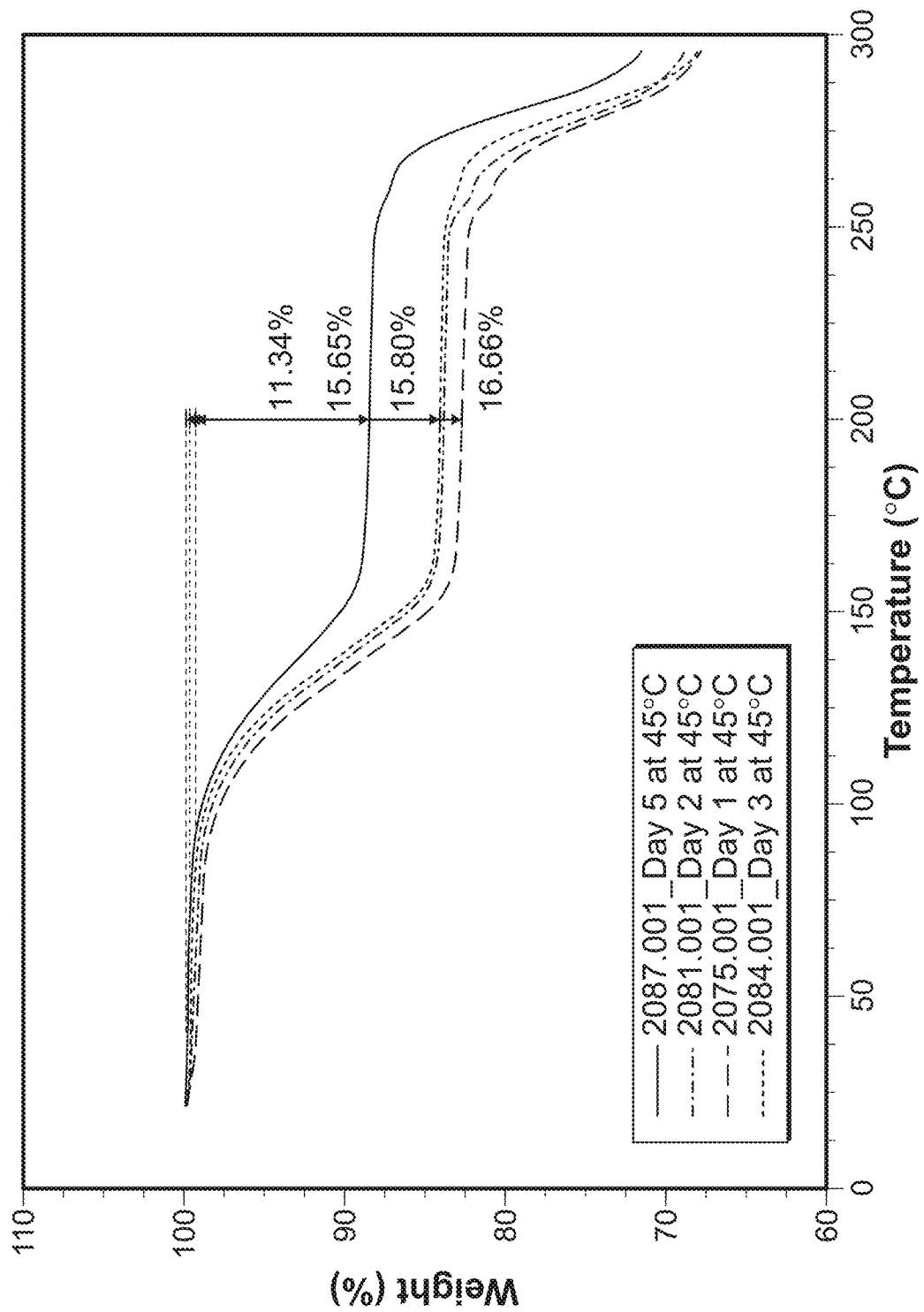
FIG. 10 is a TGA plot of crystalline solid-state Form II of DMSO solvate of RDN.

Single crystal parameters for the solid-state Form II of DMSO solvated RDN as determined by SCXRD are:

Crystal system, space group=triclinic, P1
a=4.904 (4) Å
b=9.1144 (7) Å
c=22.849 (17) Å
α=84.130 (11)°
β=99.979 (2)°
γ=89.897 (11)°
Cell Volume=1013.57 Å$^3$ The TGA plot (FIG. 10) show TGA weight loss of 16.7% from about 100-150° C. after drying for one day at 45° C. and 11.3% from about 100-150° C. after drying for five days at 45° C. for the solid-state Form II of DMSO solvate of RDN.

Figure 11:
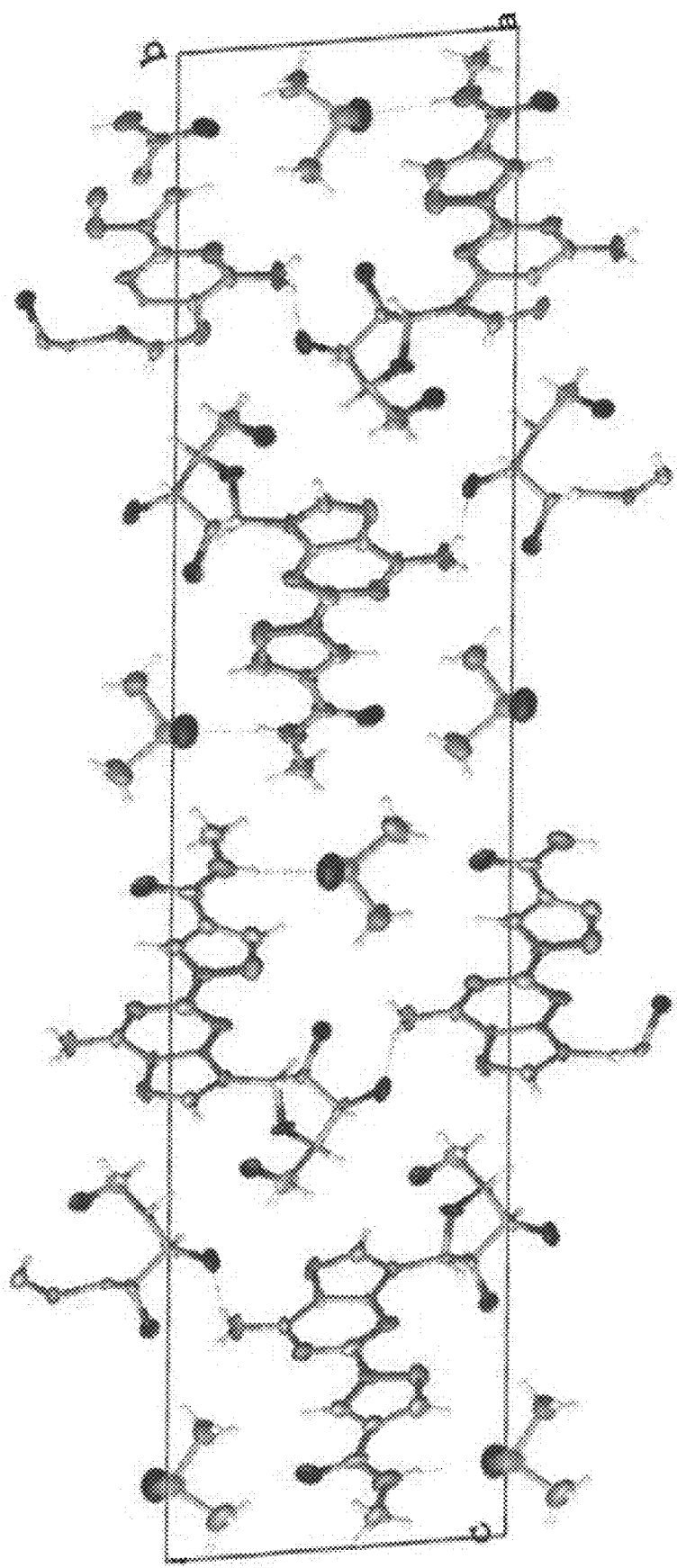
FIG. 11 shows unit cell in the crystalline solid-state Form II of DMSO solvate of RDN.

FIG. 11 shows unit cell in the crystalline solid-state Form II of DMSO solvate of RDN.

V. Solid-State Form I of Anhydrous RDN 5 g of RDN is dissolved in 20 mL of DMSO with stirring at 50° C. to yield a clear solution of RDN in DMSO, and then is sequentially added 20 mL of ethyl acetate, 0.2 g of seeds of solid-state Form II of DMSO solvate of RDN, and 80 mL of ethyl acetate. After the additions heating is stopped and solution is stirred for 5 hours. The solution is filtered, the isolated solid is split in half, and half of the solid is dried under vacuum at 60° C. to yield solid-state Form I of anhydrous RDN.

Figure 12:
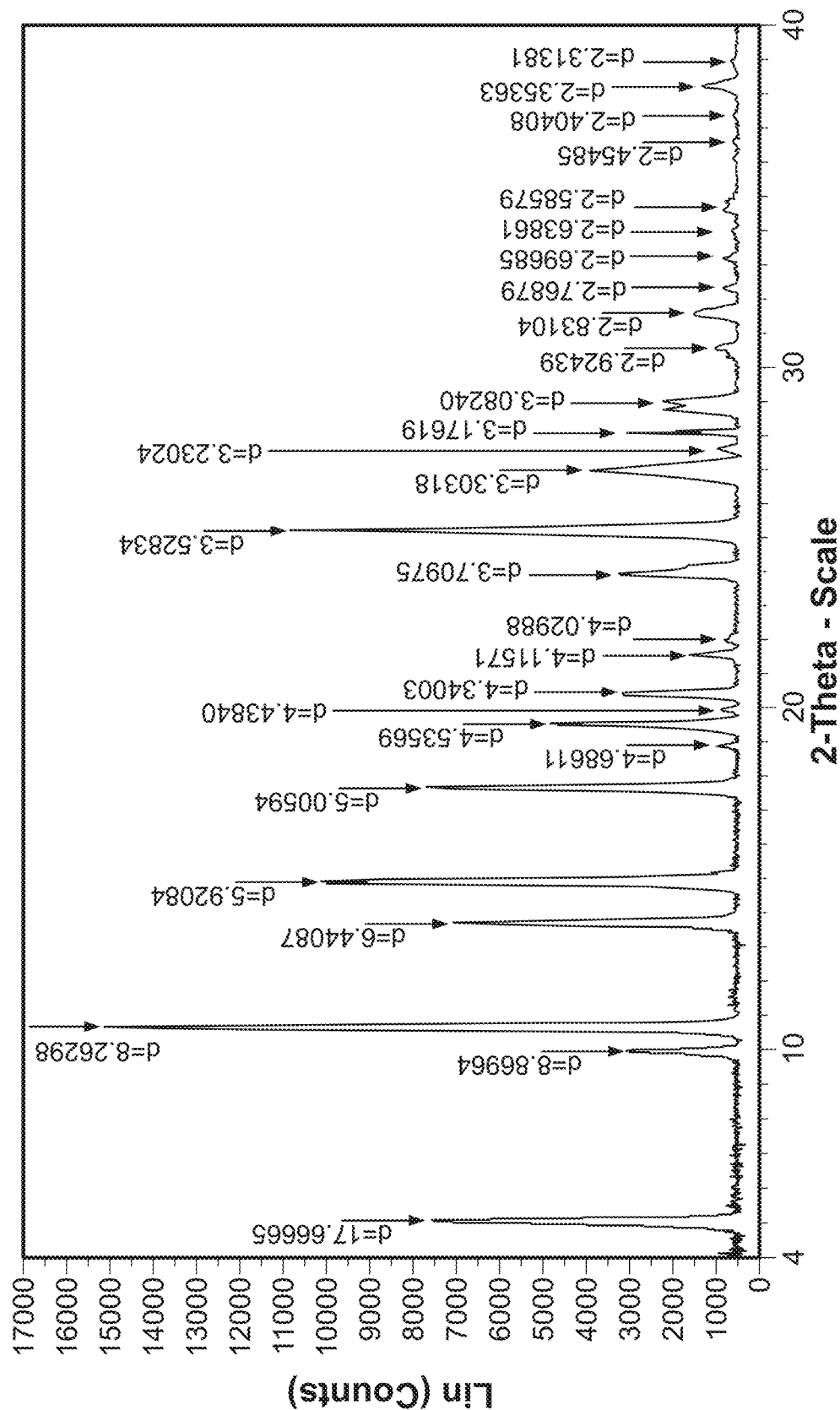
FIG. 12 is an XRPD pattern of crystalline Form I of anhydrous solid-state form of RDN.

The XRPD (FIG. 12) is directed to the solid-state Form I of anhydrous RDN, and 2Θ, d-spacing and relative % intensity values for peaks are shown in Table V.

TABLE V

| Angle 2Θ° | d value Angstrom | Intensity % |
|---|---|---|
| 5.0 | 17.667 | 49.6 |
| 10.0 | 8.870 | 19.7 |
| 10.7 | 8.263 | 100 |
| 13.7 | 6.441 | 46.8 |
| 15.0 | 5.921 | 66.8 |
| 17.7 | 5.006 | 50.3 |
| 19.6 | 4.536 | 31.6 |
| 20.5 | 4.340 | 20.8 |
| 21.6 | 4.116 | 10.6 |
| 24.0 | 3.710 | 21.2 |
| 25.2 | 3.528 | 71.4 |
| 27.0 | 3.303 | 26 |
| 28.1 | 3.176 | 19.7 |
| 28.9 | 3.082 | 14 |

The angle measurements are ±0.2° 2Θ. Key defining peaks for solid-state Form I of anhydrous RDN include 5.0, 13.7, 24.0 and 27.0.

Figure 13:
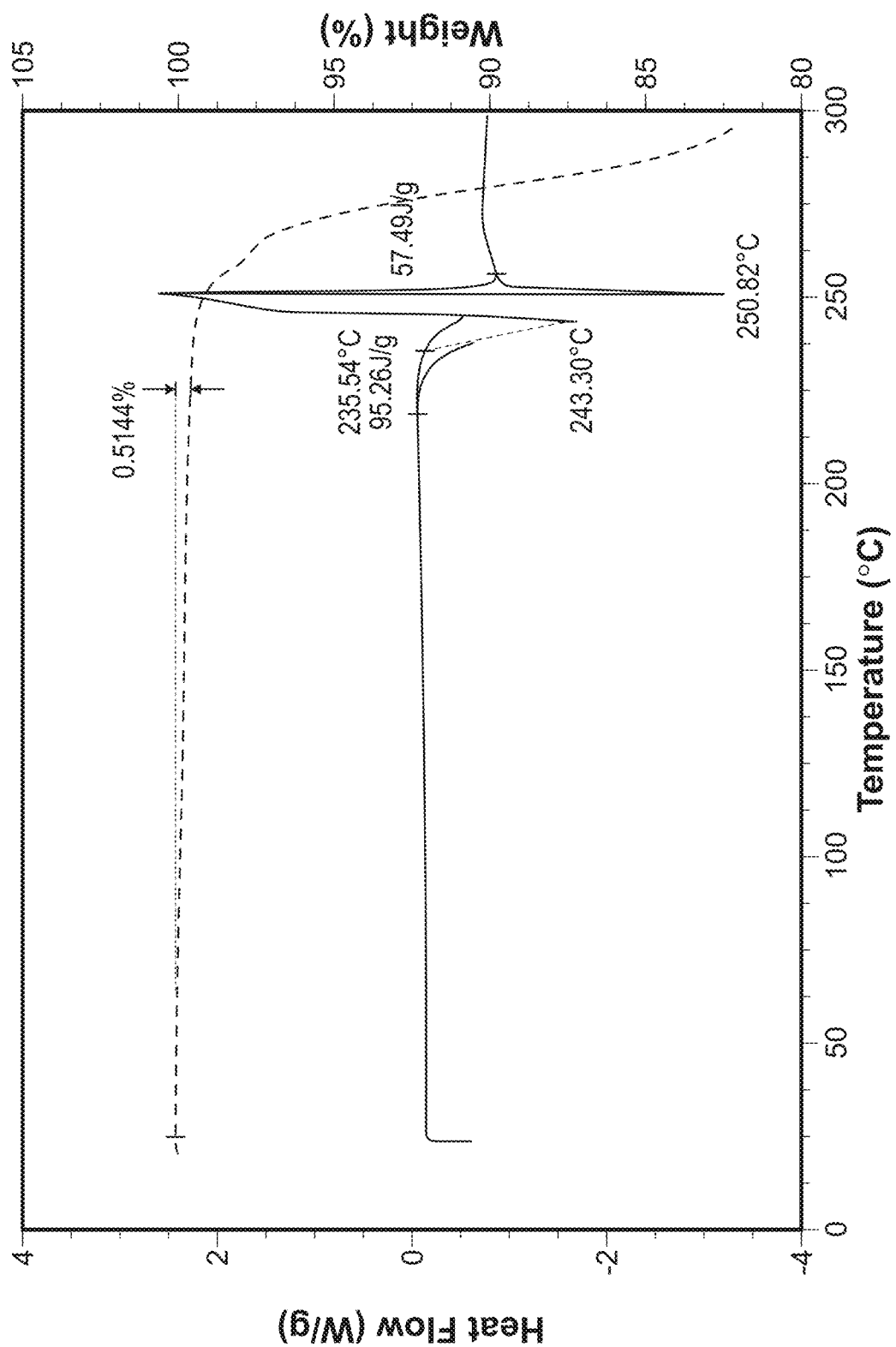
FIG. 13 is a DSC and TGA of crystalline Form I of anhydrous solid-state form of RDN.

The DSC and TGA plots (FIG. 13) show TGA weight loss of about 0.5% through about 250° C., and DSC shows thermal event at 250.8° C. for the solid-state Form I of anhydrous RDN.

Figure 14:
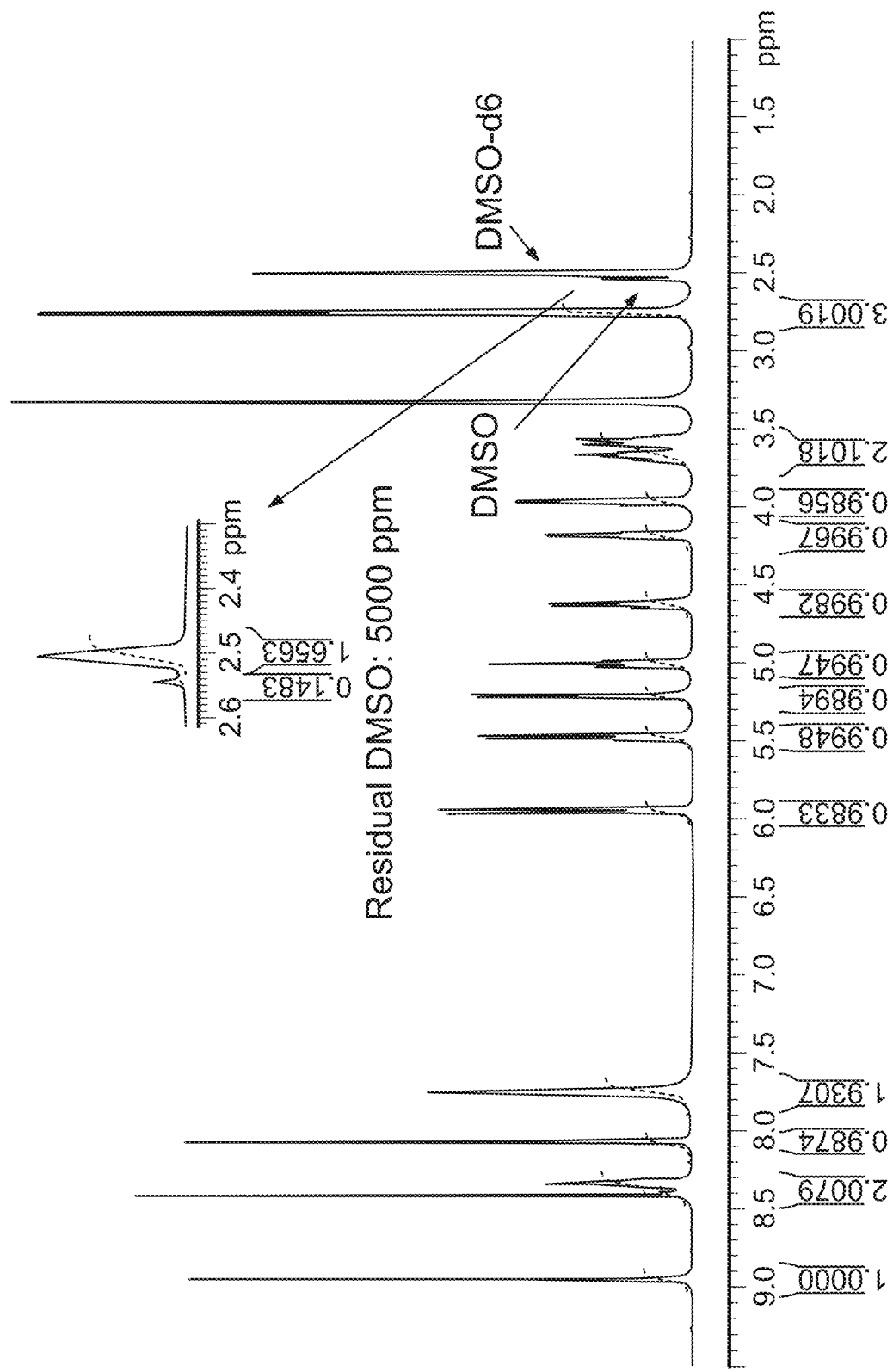
FIG. 14 is a $^1$H NMR spectra of crystalline Form I of anhydrous solid-state form of RDN.

FIG. 14 is directed to the $^1$H NMR for the solid-state Form I of anhydrous RDN.

The above description is presented to enable a person of ordinary skill in the art to make and use the various embodiments. Descriptions of specific devices, techniques, and applications are provided only as examples. Various modifications to the examples will be readily apparent to those of ordinary skill in the art, and the general principles described herein—above and after, may be applied to other examples and applications without departing from the scope of the present invention. Thus, the various embodiments are not intended to be limited to the examples described herein.

While the present invention has been described in terms of its specific embodiments, certain modifications and equivalents will be apparent to those skilled in the art and are intended to be included within the scope of the present invention.

The invention claimed is:

1. A compound which is a crystalline methanol or dimethyl sulfoxide solvate of regadenoson.

2. The compound of claim 1 which is the methanol solvate of regadenoson.

3. The compound of claim 2 wherein the methanol solvate of regadenoson is Form I of methanol solvate of regadenoson, which as a single crystal is monoclinic, C2 a=20.2462 Å b=6.9115 Å c=44.061 Å, α=90°, β=99.98°, γ=90°, unit Cell Volume is about 6072.24 Å$^3$ and having at least 2 or more X-ray powder diffraction peaks selected from about 9.1, 13.0, 14.3, 17.3, 18.2, 20.8, 24.6 and 25.5° 2θ, as measured by CuKα radiation.

4. The compound of claim 2 wherein the methanol solvate of regadenoson is Form II of methanol solvate of regadenoson, having at least 2 or more X-ray powder diffraction peaks selected from about 10.2, 12.2, 16.2, 17.9, 21.7, 26.3 and 27° 2θ, as measured by CuKα radiation and having one to three thermal event(s) selected from about 190.9° C., 205.3° C., and 277.6° C.

5. The compound of claim 1 which is the dimethyl sulfoxide solvate of regadenoson.

6. The compound of claim 5 wherein the dimethyl sulfoxide solvate of regadenoson is Form I of dimethyl sulfoxide solvate of regadenoson, which as a single crystal is orthorhombic, P2$_1$2$_1$2$_1$, a=4.9676 Å b=9.203 Å c=45.667 Å, α=90° β=90° γ=90°, unit Cell Volume is about 2087.68 Å$^3$ and having at least 2 or more X-ray powder diffraction peaks selected from about 15.6, 19.5, 20.4 and 25.4° 2θ, as measured by CuKα radiation and having one to two thermal event(s) selected from about 143.0° C. and 251.6° C.

7. The compound of claim 5 wherein the dimethyl sulfoxide solvate of regadenoson is Form II of dimethyl sulfoxide solvate of regadenoson, which as a single crystal is triclinic, P1 a=4.904 Å b=9.1144 Å c=22.849 Å, α=84.130° β=99.979° γ=89.89'7°, unit Cell Volume is about 1013.57 Å$^3$ and having at least 2 or more X-ray powder diffraction peaks selected from about 3.9, 10.1, 10.9, 16.0, 20.3 and 25.9°.

8. A compound which is a crystalline Form I of anhydrous regadenoson having at least 2 or more X-ray powder diffraction peaks selected from about 5.0, 13.7, 24.0 and 27.0° 2θ, as measured by CuKα radiation or having a thermal event at about 250.8° C.

9. A process for the preparation of the Form I of methanol solvate of regadenoson of claim 3, comprising: (a) dissolving regadenoson in methanol to form a saturated methanol solution of regadenoson; and (b) evaporating slowly the methanol solution of regadenoson to yield the Form I of methanol solvate of regadenoson.

10. A process for the preparation of the Form I of dimethyl sulfoxide solvate of regadenoson of claim 6, comprising: (a) dissolving regadenoson in dimethyl sulfoxide (about 100:1—wt(mg)$_{RDN}$:v(mL)$_{DMSO}$) to form a solution of regadenoson in dimethyl sulfoxide, (b) adding acetone to the solution of regadenoson in dimethyl sulfoxide (about 2:1—v$_{Ace}$:v$_{DMSO}$), (c) stirring the resultant solution of step (b) for about 18-20 h at about room temperature and then for about 48 h with cooling to precipitate the Form I of DMSO solvate of regadenoson.

11. A process for the preparation of the Form I of dimethyl sulfoxide solvate of regadenoson of claim 6, comprising: (a) dissolving regadenoson in dimethyl sulfoxide (about 100:1—wt(mg)$_{RDN}$:v(mL)$_{DMSO}$) to form a solution of regadenoson in dimethyl sulfoxide, (b) adding methanol or ethyl acetate to the solution of regadenoson in dimethyl sulfoxide (about 1.5:1—v$_{MeOH}$:v$_{DMSO}$) or (.about.1:1—v$_{EtOAc}$:v$_{DMSO}$), (c) stirring the resultant solution of step (b) for about 72 h at about room temperature, and (d) drying the resultant solution of step (c) under reduced pressure with warming at about 50° C. to yield the Form I of DMSO solvate of regadenoson.

12. A process for the preparation of the Form II of dimethyl sulfoxide solvate of regadenoson of claim 7, comprising: (a) dissolving regadenoson in dimethyl sulfoxide (about 210:1—wt(mg)$_{RDN}$:v(mL)$_{DMSO}$) at 50° C. to form a solution of regadenoson in dimethyl sulfoxide, (b) adding ethyl acetate to the solution of regadenoson in dimethyl sulfoxide (about 1:3—v$_{DMSO}$:v$_{EtOAc}$), (c) stirring the resultant solution of step (b) at about room temperature for about 18-20 h to yield a precipitate, and (d) filtering the precipitate, washing the filtered precipitate with ethyl acetate (about 1:1—v$_{DMSO}$:v$_{EtOAc}$) and drying the washed precipitate under vacuum at about 45° C. to yield the Form II of DMSO solvate of regadenoson.

13. A process for the preparation of the Form I of anhydrous regadenoson of claim 8 comprising: (a) dissolving regadenoson in dimethyl sulfoxide (about 250:1—wt (mg)$_{RDN}$:v(mL)$_{DMSO}$) at about 50° C. to form a solution of regadenoson in dimethyl sulfoxide, (b) adding sequentially ethyl acetate (about 1:1—V$_{DMSO}$:v$_{EtOAc}$), seeds of Form II of DMSO solvate of RDN (about 1:0.04—wt$_{RDN}$:wt$_{RDNseed}$), and ethyl acetate (about 1:4—v$_{DMSO}$:v$_{EtOAc}$) to the solution of regadenoson in dimethyl sulfoxide while maintaining the temperature at about 50° C., (c) discontinuing the heating, and stirring the resultant solution of step (b) for about 5 hrs to yield a precipitate, and (d) filtering the precipitate, and drying under vacuum at about 60° C. to yield the Form I of anhydrous regadenoson.

\* \* \* \* \*